US007059176B2

(12) United States Patent
Sparks

(10) Patent No.: US 7,059,176 B2
(45) Date of Patent: Jun. 13, 2006

(54) RESONANT TUBE VISCOSITY SENSING DEVICE

(75) Inventor: Douglas Ray Sparks, Whitmore Lake, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 0 days.

(21) Appl. No.: 10/710,106

(22) Filed: Jun. 18, 2004

(65) Prior Publication Data

US 2004/0255648 A1    Dec. 23, 2004

Related U.S. Application Data

(60) Provisional application No. 60/479,046, filed on Jun. 18, 2003.

(51) Int. Cl.
*G01N 11/16*     (2006.01)
(52) U.S. Cl. .................. 73/54.41; 73/54.01; 73/54.02
(58) Field of Classification Search .............. 73/54.01, 73/54.02, 54.41, 54.42
See application file for complete search history.

(56) References Cited

U.S. PATENT DOCUMENTS

| | | | | |
|---|---|---|---|---|
| 5,827,979 | A | * | 10/1998 | Schott et al. .......... 73/861.357 |
| 6,006,609 | A | * | 12/1999 | Drahm et al. .......... 73/861.357 |
| 6,311,549 | B1 | | 11/2001 | Thundat et al. ............. 73/54.24 |
| 6,477,901 | B1 | * | 11/2002 | Tadigadapa et al. ... 73/861.352 |
| 6,647,778 | B1 | * | 11/2003 | Sparks .................... 73/204.26 |
| 2001/0039829 | A1 | * | 11/2001 | Wenger et al. ............. 73/54.41 |

OTHER PUBLICATIONS

"Quality Factors of MEMS Gyros and The Role of Thermoelastic Damping"; Amy Duwel, Marcie Weinstein, John Gorman, Jeff Borenstein, Paul Ward; The Draper Laboratories & the Massachusetts Institute of Technolgoy, Cambridge, MA.
"Wafer-to-Wafer Bonding of Nonplanarized MEMS Surfaces Using Solder"; D. Sparks, G. Queen, R. Weston, G. Woodward, M. Putty, L. Jordan, S. Zarabadi, K. Jayakar; Journal of Micromechanics and Microengineering, 11 (2001) pp. 630-634.
"Plasma Etching of Si, $SiO_2$, $Si_3N_4$, and Resist with Fluorine, Chlorine, and Bromine Compounds"; Douglas R. Sparks; The Electrochemical Society, Inc.; J. Electrochem. Soc., vol. 139, No. 6, Jun. 1992.
"Fluid Density Sensor Based on Resonance Vibration"; Peter Enoksson, Goran Stemme, Erik Stemme; Sensors and Actuators, A 46-47 (1995) 327-331.

* cited by examiner

*Primary Examiner*—Daniel S. Larkin
(74) *Attorney, Agent, or Firm*—Gary M. Hartman; Domenica N. S. Hartman; Hartman & Hartman

(57) ABSTRACT

A method and device for assessing the viscosity of a fluid. The method and device utilize a tube with a vibrating freestanding portion into which the fluid is introduced, and relies on sensing the influence that the fluid has on the vibrational movement of the tube to assess the viscosity of the fluid. For this purpose, the freestanding portion is preferably driven at or near a resonant frequency, movement of the freestanding portion is sensed, and the viscosity of a fluid within the tube is assessed by ascertaining the damping effect the fluid has on movement of the freestanding portion at or near the resonant frequency.

39 Claims, 3 Drawing Sheets

RESONANT TUBE VISCOSITY SENSING DEVICE

CROSS REFERENCE TO RELATED APPLICATIONS

This application claims the benefit of U.S. Provisional Application No. 60/479,046, filed Jun. 18, 2003.

FEDERAL RESEARCH STATEMENT

[Federal Research Statement Paragraph]This invention was made with Government support under Agreement No. 70NANB3H3040 awarded by NISTATP. The Government has certain rights in the invention.

BACKGROUND OF INVENTION

FIELD OF THE INVENTION

The present invention generally relates to devices and methods for measuring properties of fluids. More particularly, this invention relates to a sensing device equipped with a resonating tube through which a fluid flows for sensing viscosity and other rheological properties of the fluid.

DESCRIPTION OF THE INVENTION

Viscosity is the internal resistance to flow exhibited by a fluid, and is a key fluid parameter for a variety of fluids, including lubricants, adhesives, paints, oils, tars, electrophoresis gels, syrups and fuels. Lubricants and particularly automotive engine oils are notable examples of fluids whose viscosities change over time, to the detriment of the components they lubricate. While oil quality sensors based on measuring the dielectric constant or electrical resistance of a lubricant have been developed and are commercially available, viscosity provides a better indication of the condition of an oil (and other lubricant) and when the oil should be replaced. Consequently, there has been an effort to develop viscosity sensors for engine oil applications.

Various methods have been developed to measure viscosity, including capillary force, moving paddles, blades, vibrating tuning forks, and hollow tubes or cantilevers immersed in a fluid. More recently, rheometers and viscometers have been developed with a vibrating micromachined silicon cantilever that is immersed in the fluid of interest, with the resultant damping of the cantilever vibration being used to indicate viscosity.

The above-noted prior art relying on vibrating structure requires insertion of the vibrating structure into the fluid so that the fluid surrounds the structure. In contrast, commonly-assigned U.S. Pat. No. 6,647,778 to Sparks discloses a sensing device capable of sensing the viscosity of a fluid flowing through a microelectromechanical system (MEMS). Sparks' sensing device is used in combination with a micromachined resonating tube, preferably of the type disclosed in commonly-assigned U.S. Pat. No. 6,477,901 to Tadigadapa et al. and adapted for resonant sensing of mass flow and density of a fluid flowing through the tube. One embodiment of Sparks' sensing device incorporates second and third micromachined tubes having bridge portions adapted to deflect in response to a pressure change of the fluid flowing therethrough. Sparks ascertains the viscosity of the fluid flowing through the tubes by comparing the pressures of the fluid within the second and third tubes.

SUMMARY OF INVENTION

The present invention provides a method and device for assessing the viscosity and optionally additional rheological properties of a fluid. The invention utilizes a vibrating tube into which the fluid is introduced, and relies on sensing the influence that the fluid has on the vibrational movement of the tube to assess the viscosity of the fluid.

More particularly, the method of this invention entails introducing a fluid of interest into a passage within a freestanding portion of a tube, vibrating the freestanding portion of the tube at or near a resonant frequency thereof, sensing movement of the freestanding portion of the tube, and then assessing the viscosity of the fluid by ascertaining the damping effect the fluid has on the vibrational movement of the freestanding portion at or near the resonant frequency.

The viscosity sensing device of this invention comprises a tube supported by a substrate and comprising a fluid inlet, a fluid outlet, and a freestanding portion between the fluid inlet and outlet so as to define a continuous passage Through the tube. The freestanding portion is spaced apart from a surface of the substrate, and means is provided for vibrating the freestanding portion of the tube at or near a resonant frequency thereof. Means is also provided for sensing movement of the freestanding portion of the tube, and for assessing the viscosity of a fluid within the tube by ascertaining the damping effect the fluid within the freestanding portion has on the vibrational movement of the freestanding portion at or near the resonant frequency.

In view of the above, it can be seen that the present invention provides a method and device by which viscosity of a fluid is sensed by flowing the fluid through a vibrating tube, as opposed to immersing the vibrating tube in the fluid. The damping effect that the fluid has on the vibrational movement of the tube can be ascertained in reference to, for example, the quality (Q) factor or peak amplitude of the freestanding portion at the resonant frequency, or an amplitude-versus-frequency plot of the freestanding portion in the vicinity of the resonant frequency. Various operating modes can be employed to sense the influence that the fluid viscosity has on the vibrating tube. For example, the device can be continuously operated to sense changes in the damping effect that occur over time as a result of changes in viscosity of the fluid, or the device can be operated intermittently to sense the influence that the fluid viscosity has on the decay of the vibrational movement of the tube. Advantageously, the device can be fabricated from a variety of materials using micromachining processes, enabling miniaturization of the device.

Other objects and advantages of this invention will be better appreciated from the following detailed description.

DETAILED DESCRIPTION

Figure 1:
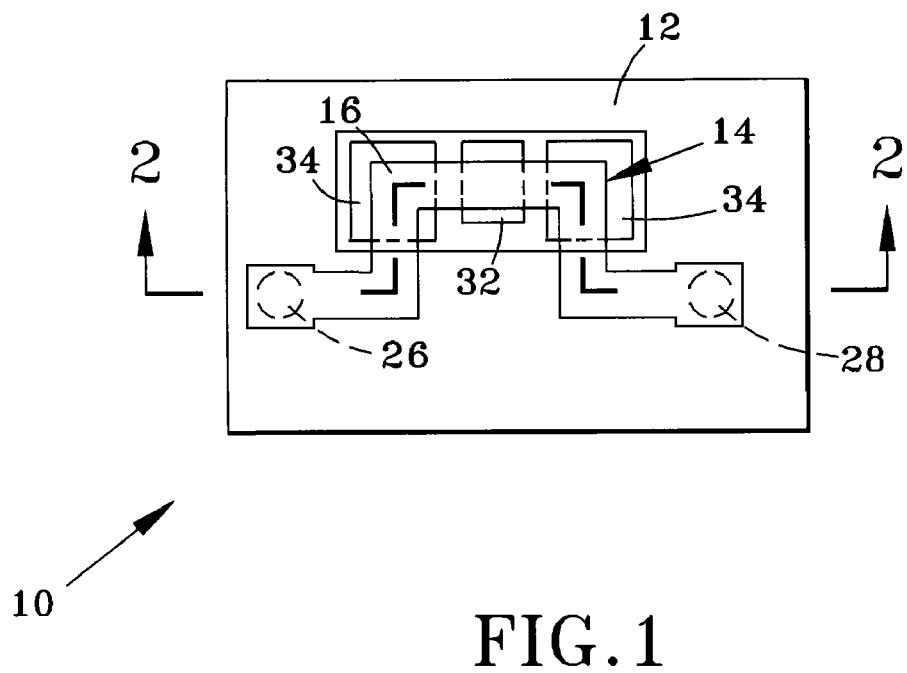
FIGS. 1 and 2 are plan and cross-sectional views, respectively, of a viscosity sensing device with a micromachined tube through which a fluid of interest flows in accordance with an embodiment of this invention.
Figure 2:
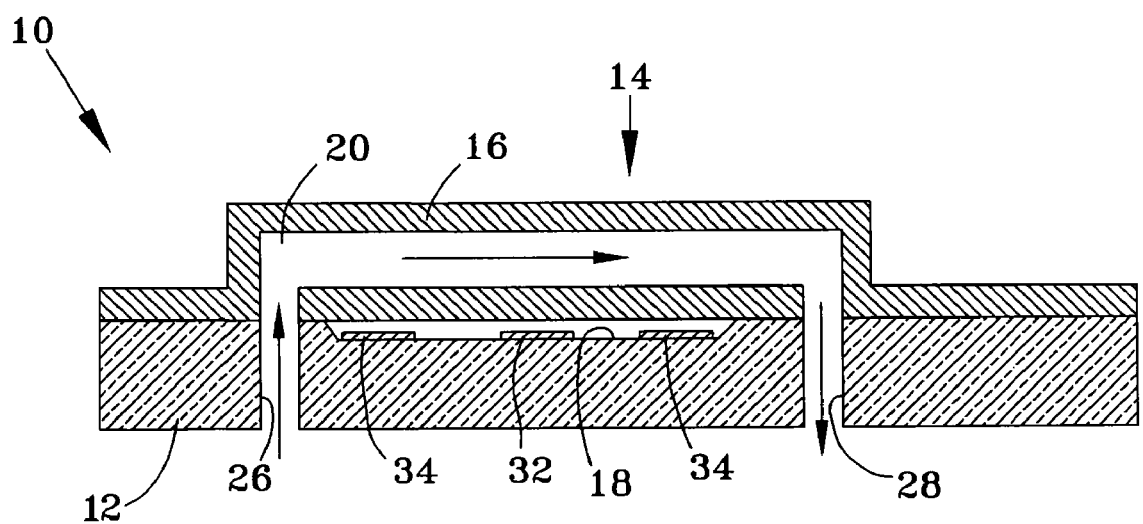

FIGS. 1 and 2 represent a viscosity sensing device 10 in accordance with an embodiment of the present invention. The device 10, which may be termed a rheometer or viscometer, is represented as being fabricated on a substrate 12, which can be formed of silicon or another semiconductor material, quartz, glass, ceramic, metal, or a composite material. A tube 14 is supported by the substrate 12 so as to have a freestanding portion 16 suspended above a surface 18 of the substrate 12, depicted in FIGS. 1 and 2 as being defined by a recess in the substrate 12. The freestanding portion 16 of the tube 14 is generally U-shaped, though other shapes—both simpler and more complex—are within the scope of this invention. The tube 14 defines a passage 20 through which a fluid can flow. Fluid is able to enter the device 10 through a fluid inlet 26 and exits the tube 14 through a fluid outlet 28, both of which are represented in FIG. 2 as being etched or otherwise formed in a surface of the substrate 12 opposite the tube 14.

According to a preferred aspect of the invention, the tube 14 is micromachined from silicon or another semiconductor material, quartz, glass, ceramic, metal or composite material. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. The tube 14 can either be fabricated entirely from layers of the chosen materials deposited on the substrate 12, or fabricated in part by etching the substrate 12. The shape and size of the tube 14 can be chosen to provide an adequate flow capacity for the fluid and to have suitable vibration parameters for the intended fluids to be evaluated with the device 10. Because micromachining technologies are employed to fabricate the tube 14, the size of the tube 14 can be extremely small, such as lengths of about 0.5 mm and cross-sectional areas of about 250 $\mu m^2$, with smaller and larger tubes also being within the scope of this invention. Particularly suitable processes for fabricating resonant mass flow and density sensors using silicon micromachining techniques are disclosed in commonly-assigned U.S. Pat. No. 6,477,901 to Tadigadapa et al., incorporated herein by reference, which uses wafer bonding and silicon etching techniques to produce a suspended silicon tube on a wafer. The tube is vibrated at or near resonance to determine the mass flow rate and density of a fluid flowing through the tube using Coriolis force principles.

The invention can also make use of Coriolis force principles, though for the purpose of ascertaining the viscosity of a fluid within the tube 14. In the embodiment shown in FIGS. 1 and 2, the freestanding portion 16 is vibrated in a direction perpendicular to the surface 18 of the substrate 12 (into the plane of FIG. 1), preferably at or near its resonant frequency. During half of the vibration cycle in which the tube 14 moves upward, the freestanding portion 16 has upward momentum as the fluid travels around the tube bends, and the fluid flowing out of the freestanding portion 16 resists having its vertical motion decreased by pushing up on that part of the freestanding portion 16 nearest the fluid outlet 28. The resulting force causes the freestanding portion 16 of the tube 14 to twist. As the tube 14 moves downward during the second half of its vibration cycle, the freestanding portion 16 twists in the opposite direction. This twisting characteristic is referred to as the Coriolis effect, and the degree to which the freestanding portion 16 of the tube 14 deflects during a vibration cycle as a result of the Coriolis effect can be correlated to the mass flow rate of the fluid flowing through the tube 14, while the density of the fluid is proportional to the frequency of vibration.

The tube 14 is preferably driven at or near resonance, with the resonant frequency of the tube 14 being controlled by its mechanical design (shape, size, construction and materials). Resonant frequencies will generally be in the range of about 1 kHz to about 100 kHz. The amplitude of vibration is preferably adjusted through means used to vibrate the tube 14. As shown in FIGS. 1 and 2, a drive electrode 32 is located beneath the tube 14 on the surface 18 of the substrate 12. As depicted in FIGS. 1 and 2, the tube 14 is formed of an electrically-conductive material, such as doped silicon, and can therefore serve as an electrode that can be capacitively coupled to the drive electrode 32, enabling the electrode 32 to electrostatically drive the tube 14. However, it is foreseeable that the tube 14 could be formed of a nonconductive material, and a separate electrode formed on the tube 14 opposite the electrode 32 for vibrating the tube 14 electrostatically. An alternative driving technique is to provide a piezoelectric element on an upper surface of the tube 14 to generate alternating forces in the plane of the tube 14 that flex the freestanding portion 16 of the tube 14 in directions normal to the plane of the tube 14. Other alternatives are to drive the freestanding portion 16 of the tube 14 magnetically, thermally, piezoresistively, thermally, optically, or by another actuation technique. Also shown in FIGS. 1 and 2 are sensing electrodes 34 for providing feedback to the drive electrode 32 to enable the vibration frequency to be controlled with appropriate circuitry (not shown) while also sensing the deflection of the tube 14 relative to the substrate 12. The sensing electrodes 34 can sense the tube 14 capacitively, electrostatically, magnetically, piezoelectrically, piezoresistively, thermally, optically, or in any other suitable manner capable of sensing the proximity or motion of the tube 14.

Figure 3:
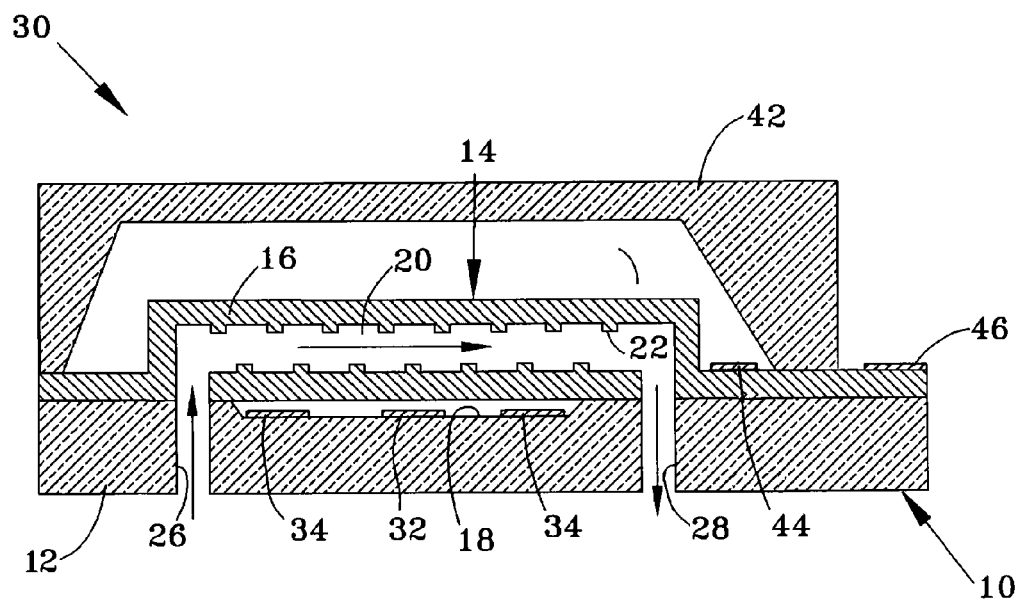
FIG. 3 is a cross-sectional view of a sensor package that makes use of the viscosity sensing device of FIGS. 1 and 2.

In FIG. 3, the sensing device 10 is shown enclosed by a cap 42 to form a sensing package 30. The cap 42 allows for vacuum packaging that reduces air damping of the tube vibration, as will be discussed below. A variety of package and wafer-level methods exist to vacuum package devices. These include solder or weld hermetic packages, and wafer bonding using glass frit, solder, eutectic alloy, adhesive, and anodic bonding. A preferred material for the cap 42 is silicon, allowing silicon-to-silicon bonding techniques to be used. Input and output signals to the device 10 are made through bond pads 46 (only one of which is shown) outside the cap 42. Since metal runners are used to transmit the electrical signals, and the capacitive signals produced by the tube 14 are relatively small, wafer to wafer bonding methods are preferred. Therefore, in the preferred embodiment of this invention, the bond between the cap 42 and the substrate 12 is hermetic, and the enclosure formed by the substrate 12 and cap 42 is evacuated to enable the tube 14 to be driven efficiently at high quality (Q) values without damping. In such an embodiment, a getter material is preferably placed in the enclosure to assist in reducing and maintaining a low cavity pressure. As an alternative to a hermetically sealed package, the tube 14 could be enclosed such that a vacuum can be drawn when desired through the use of a pump.

In an investigation leading to the invention, it was observed that a hollow resonating silicon tube used in accordance with Tadigadapa et al. to sense density and flow rate exhibited significant changes in the quality factor of the tube when filled with water or isopropyl alcohol. The peak amplitude of vibration was also observed to drop due to the presence of a fluid in the tube. From this observation, it was determined that the viscosity of a fluid within a micromachined resonating tube sufficiently influences the vibrational movement of the tube to permit quantifying and qualifying the viscosity of the fluid.

As known in the art, the quality factor is a dimensionless parameter reflecting energy stored to energy lost in each cycle of an oscillation of a vibrating structure. The quality factor of a given structure is inversely related to the damping factor associated with the structure, and generally relates to the sharpness or width of the response curve in the vicinity of a resonant frequency of the vibrating structure. One method of determining the quality factor of a resonating structure is to divide the value of the peak frequency of the structure by the bandwidth at 3 db below the peak. The components of a vibrating system, such as the device 10 shown in FIGS. 1 through 3, contribute to the quality factor of the system, namely, the electronic drive and sensing circuitry of the device 10, the material properties of the resonating tube 14 including grain boundary and defect losses, the damping of fluid (air) surrounding the tube 14, the anchor design of the tube 14, and as noted above, the damping effect of the fluid within the tube 14. Mathematically, the total quality factor of the system can be expressed as follows:

$$1/Q = 1/Q_{el} + 1/Q_{mat} + 1/Q_{ext} + 1/Q_{anchor} + 1/Q_{fluid}$$

The electronic component ($Q_{el}$) is usually very high, often greater than one million. The material component ($Q_{mat}$) is generally in the range of about 30,000 to about 200,000 if the tube 14 is formed of silicon or glass, and generally in the range of about 1000 to about 3000 if the tube 14 is formed of a metal such as nickel. The component attributable to the mechanical design of the tube anchor ($Q_{anchor}$) is often greater than 250,000. Because of the inverse relationship on which the overall quality factor of a system is calculated, the electrical, material and anchor components can be seen to have minimal impact on the overall quality factor of a micromachined resonating tube of the type described above. On the other hand, the external component ($Q_{ext}$) can be in a range of about 25 to about 200 if the damping medium is air, which would result in the external component dominating the quality factor of the total system. For this reason, vacuum packaging is preferably employed, such as that achieved with the package 30 of FIG. 3.

Finally, the component ($Q_{fluid}$) attributable to the presence of a liquid within the micromachined resonating tube 14 of this invention has been determined to have a value of about 1000. As such, for a vacuum packaged, single-crystal micromachined silicon or glass tube, damping attributable to a fluid within the tube 14 dominates the total quality factor of the system. Because damping is related to the molecular interactions in a solid or fluid, and molecular interactions is a function of the viscosity of a fluid, the quality factor of the device 10 represented in FIGS. 1 through 3 can be used to indicate and measure the viscosity of a fluid within the tube 14. The ability to determine the viscosity of a fluid within the tube 14 is independent of whether the fluid is flowing or not. In a static system in which the fluid is introduced and thereafter retained within the tube 14, viscosity can be measured in accordance with this invention, and density can be measured in accordance with the teachings of Tadigadapa et al. In a dynamic system in which the fluid flows through the tube 14, flow rate can also be measured in accordance with the teachings of Tadigadapa et al.

The configuration and etching of the tube 14 through which the fluid flows can be modified to increase the damping effect of the fluid, and thereby improve the performance of the device 10. For example, if the tube 14 is fabricated by plasma etching, a two-step etch and passivation process often used in micromachining techniques can be adjusted to scallop the sidewalls of the tube 14. Alternatively, FIG. 3 shows the passage 20 of the tube 14 as having sidewall protrusions 22. In either case, these features behave as turbulators to increase drag of the fluid flowing through the passage 20 and increase the interaction of fluidic molecules during vibration, thereby improving the accuracy of the device 10. Increasing the percentage of the cross-sectional area of the freestanding portion 16 of the tube 14 also has the capability of increasing the sensitivity of the device 10.

Because viscosity is influenced by fluid temperature, the device 10 is shown in FIG. 3 as being equipped with a sensor 44 for measuring the temperature of the fluid flowing through the tube 14. The fluid temperature will also influence the Young's and shear moduli of the materials from which the tube 14 is fabricated, causing the resonant frequency of the tube 14 to shift. By sensing the temperature of the tube 14, and therefore effectively the fluid within the tube 14, appropriate signal processing can be performed on the output of the device 10 to compensate for these temperature effects. The temperature sensor 44 can be in the form of one or more metal layers, such as a resistivesensor 44 formed by a thin-film metal layer of platinum, palladium or nickel in accordance with known practices. While shown as being placed on a deposited layer from which the tube 14 is micromachined, the sensor 44 could be placed elsewhere, such as on the cap 42.

Figure 5:
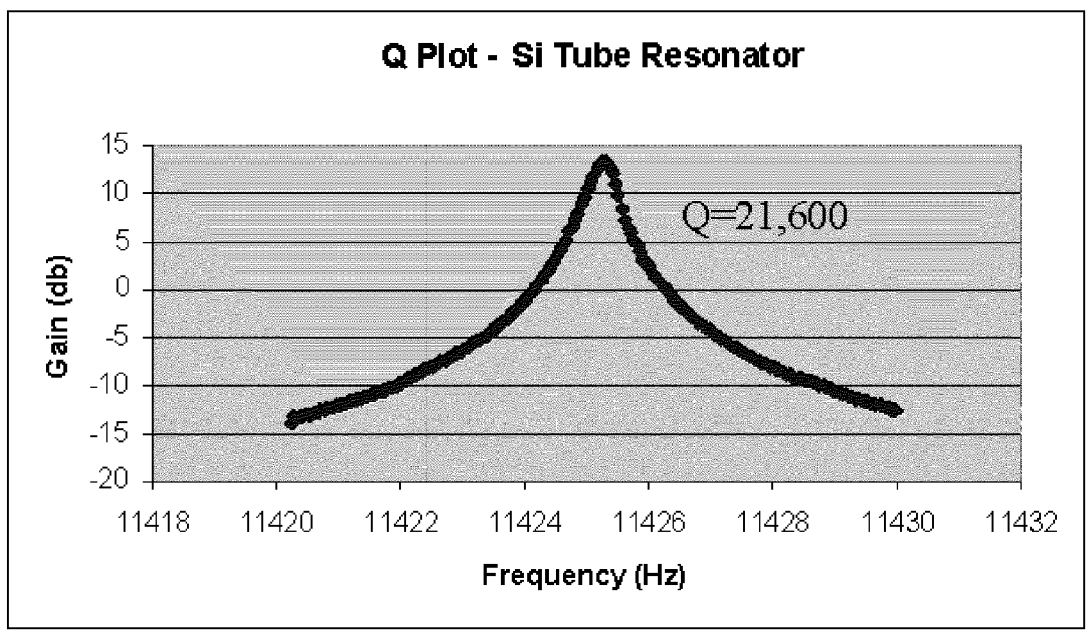
FIG. 5 is an amplitude-versus-frequency plot representative of the output of the device of FIGS. 1 through 3.

As noted above, the quality factor of the vibrating tube 14 can be measured by taking the resonant peak frequency and dividing this number (in Hertz) by the bandwidth of the peak at 3 db below the peak. For example, FIG. 5 is a amplitude-versus-frequency plot of a micromachined silicon tube of the type shown in FIGS. 1 through 3. The resonant peak frequency is approximately 11425.3, and the bandwidth at 3 db below the peak amplitude (about 14 db) is about 0.53 Hz, resulting in a quality factor of about 21,600. Other methods of measuring the quality factor or quantifying the sharpness of the resonant peak can be employed. Alternatively, changes in the magnitude of the amplitude peak could be measured to indicate the viscosity of the fluid and/or any changes in viscosity over time, and changes in the quality factor or amplitude of different resonant nodes could be compared to measured to indicate viscosity.

Figure 4:
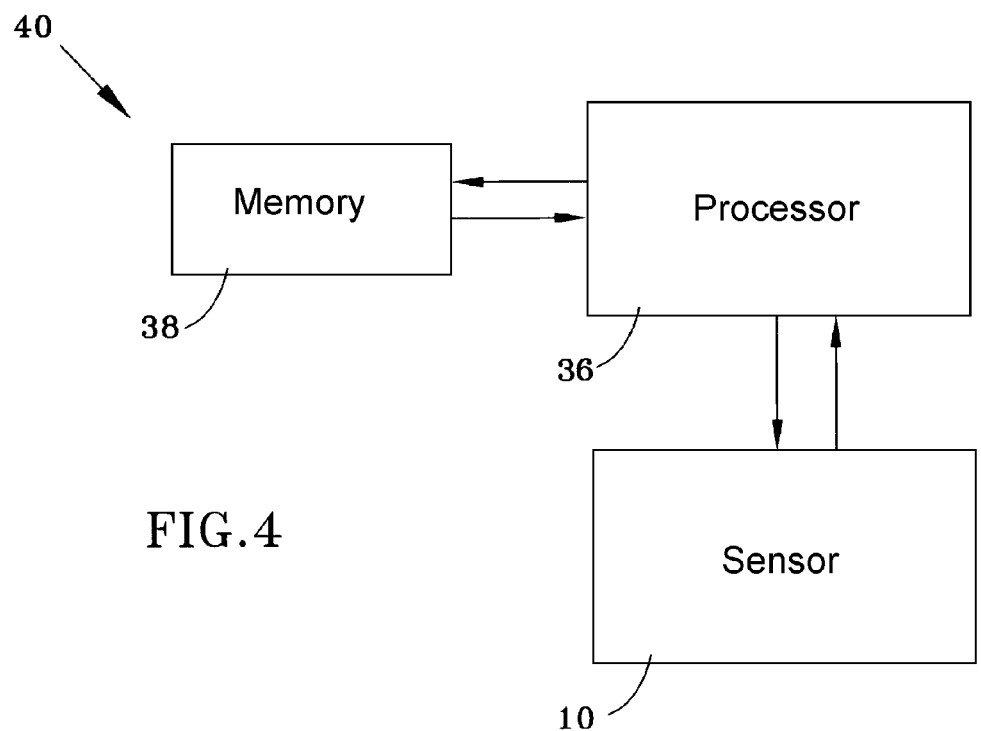
FIG. 4 schematically represents a viscosity sensing system that makes use of the sensing device of FIGS. 1 and 2.

FIG. 4 schematically represents a viscosity monitoring/measuring system 40 in which the device 10 of FIGS. 1 through 3 is employed. The system 40 includes a suitable processor 36 for sending control signals to the device 10 and processing the output of the device 10 to determine the viscosity of the fluid being examined using theoretical or empirical data. The system 40 further includes a memory device 38 in communication with the processor 36, by which data can be stored quantifying the movement of the freestanding portion 16 near the resonant frequency. For example, a calculated value of the quality factor of the tube 14 can be compared with a previously stored quality factor value, or stored for comparison to a subsequently calculated quality factor. Alternatively or in addition, the memory device 38 can store the value of the peak amplitude of the freestanding portion 16, and compare this value with a previously stored peak amplitude value. Another alternative is to compare the amplitude-versus-frequency plot of the device 10 to a stored amplitude-versus-frequency plot. Since viscosity is dominated by intermolecular interactions, different types of fluids (polar, nonpolar, organic) will respond differently to the vibrating environment of the tube 14. With this in mind, an accurate viscosity sensing device capable of use with a variety of different fluids can be achieved using appropriate calibration standards. In the system 40 depicted in FIG. 4, the memory device 38 can be used to store data pertaining to the vibrational amplitude impact of standard fluids in a look-up table or family of curves, against which the sensed behavior of a tested fluid can be compared. If the type of fluid under test is known, the best family of curves or the appropriate look-up table can be selected from the memory device 38 to more accurately determine the viscosity of the fluid under test.

The quality factor can be measured by observing the decay of intermittently-induced resonant vibrations in the tube 14, or by steady-state data collecting by which trends in the viscosity of the fluid can be continuously observed. Because most resonating structures exhibit resonant peaks at different frequencies, these multiple resonant peaks can be employed to gather additional viscosity information on a fluid. For example, such information can include the variation of viscosity with shear rate.

In view of the above, the device 10 of this invention is able to estimate the viscosity of a fluid as well as detect changes in viscosity that may occur, such as when a lubricant breaks down over time. In the case of an automotive engine, monitoring of the engine oil in this manner can be used to indicate when an oil change is needed. Historical data can be saved and compared to real-time data to determine if the lubricant has degraded and needs changing. The sensor can be integrated with an oil filter so that the oil is filtered before testing to prevent particles from clogging the small diameter tube 14. The entire sensor package can be made thin, permitting its mounting to the engine with the same threaded connection used by the oil filter. Such a capability enables the sensor package to be installed as an aftermarket sensor module for truck and automotive applications. By also monitoring the resonant frequency of the tube 14, the density of the lubricant can be determined and used to indicate whether coolant or fuel has leaked into the oil. In addition to improving the accuracy of viscosity and density measurements, the temperature sensor 44 can be employed to monitor the engine or lubricant temperature. By further monitoring the flow rate through the tube 14, the device 10 can be used to indicate clogging of coolant or lubricant lines.

While the invention has been described in terms of certain embodiments, it is apparent that other forms could be adopted by one skilled in the art. Therefore, the scope of the invention is to be limited only by the following claims.

The invention claimed is:

1. A viscosity sensing device comprising:
   a substrate;
   a micromachined tube supported by the substrate and comprising a fluid inlet, a fluid outlet, and a freestanding portion between the fluid inlet and the fluid outlet so as to define a continuous passage through the tube, the freestanding portion being spaced apart from a surface of the substrate;
   means for vibrating the freestanding portion of the tube at or near a resonant frequency thereof;
   means for sensing movement of the freestanding portion of the tube; and
   means for assessing the viscosity of a fluid within the tube by ascertaining the damping effect the fluid within the freestanding portion has on movement of the freestanding portion at or near the resonant frequency;
   wherein the viscosity sensing device is installed on an engine and the fluid is a lubricating oil within the engine.

2. A viscosity sensing device according to claim 1, further comprising means for storing data pertaining to the movement of the freestanding portion at or near the resonant frequency.

3. A viscosity sensing device according to claim 2, wherein the assessing means ascertains the damping effect by calculating the value of the quality factor of the freestanding portion while vibrating at or near the resonant frequency and comparing the calculated value of the quality factor with a quality factor value stored in the storing means.

4. A viscosity sensing device according to claim 2, wherein the assessing means ascertains the damping effect by measuring the value of the peak amplitude of the freestanding portion while vibrating at or near the resonant frequency and comparing the measured value of the peak amplitude with a peak amplitude value stored in the storing means.

5. A viscosity sensing device according to claim 2, wherein the assessing means ascertains the damping effect by comparing an amplitude-versus-frequency plot of the freestanding portion with an amplitude-versus-frequency plot stored in the storing means.

6. A viscosity sensing device according to claim 1, wherein the assessing means estimates the viscosity of the fluid.

7. A viscosity sensing device according to claim 1, wherein the assessing means is operable to intermittently assess the viscosity of the fluid within the tube.

8. A viscosity sensing device according to claim 1, wherein the assessing means is operable to continuously assess the viscosity of the fluid within the tube.

9. A viscosity sensing device according to claim 1, wherein the fluid flows through the tube during operation of the assessing means.

10. A viscosity sensing device according to claim 9, further comprising means for determining the mass flow rate of the fluid flowing through the tube by sensing a Coriolis force-induced twisting of the freestanding portion.

11. A viscosity sensing device according to claim 9, further comprising means for determining the density of the fluid flowing through the tube by sensing changes in the resonant frequency of the freestanding portion.

12. A viscosity sensing device according to claim 1, wherein the fluid does not flow through the freestanding portion during operation of the assessing means.

13. A viscosity sensing device according to claim 1, further comprising means for sensing the temperature of the fluid in the freestanding portion.

14. A viscosity sensing device according to claim 1, wherein the freestanding portion is a cantilevered portion of the tube above the surface of the substrate, and the vibrating means and the movement sensing means are electrodes on the surface of the substrate beneath the cantilevered portion of the tube.

15. A viscosity sensing device according to claim 1, further comprising a cap hermetically bonded to the substrate so as to define a hermetically-sealed evacuated enclosure containing the freestanding portion.

16. A viscosity sensing device according to claim 1, wherein the tube comprises flow turbulators that extend into the passage within the freestanding portion.

17. A viscosity sensing device according to claim 1, wherein the tube is formed of semiconducting material.

18. A viscosity sensing device according to claim 1, wherein the fluid flows through the tube during operation of the assessing means, and the device further comprises means for determining the mass flow rate of the fluid flowing through the tube by sensing a Coriolis force-induced twisting of the freestanding portion, means for determining the density of the fluid flowing through the tube by sensing changes in the resonant frequency of the freestanding portion, and means for sensing the temperature of the fluid in the freestanding portion.

19. A viscosity sensing device comprising:
a substrate;
a micromachined tube supported by the substrate and comprising a fluid inlet, a fluid outlet, and a freestanding portion between the fluid inlet and the fluid outlet so as to define a continuous passage through the tube, the freestanding portion being spaced apart from a surface of the substrate;
means for vibrating the freestanding portion of the tube at or near a resonant frequency thereof;
means for sensing movement of the freestanding portion of the tube; and
means for assessing the viscosity of a fluid within the tube by ascertaining the damping effect the fluid within the freestanding portion has on movement of the freestanding portion at or near the resonant frequency;
wherein the fluid flows through the tube during operation of the assessing means, and the device further comprises means for determining the mass flow rate of the fluid flowing through the tube by sensing a Coriolis force-induced twisting of the freestanding portion, means for determining the density of the fluid flowing through the tube by sensing changes in the resonant frequency of the freestanding portion, and means for sensing the temperature of the fluid in the freestanding portion; and
wherein the device is a component of a lubrication system, the fluid is a lubricant, and the device uses the viscosity, the mass flow rate, the density, and the temperature of the lubricant to indicate the condition of the lubricant and the lubrication system.

20. A method of assessing the viscosity of a fluid, the method comprising the steps of:
introducing the fluid into a passage within a freestanding portion of a micromachined tube;
vibrating the freestanding portion of the tube at or near a resonant frequency thereof;
sensing movement of the freestanding portion of the tube; and
assessing the viscosity of a fluid within the tube by ascertaining the damping effect the fluid within the freestanding portion has on movement of the freestanding portion at or near the resonant frequency;
wherein the damping effect is ascertained by one of the following:
measuring the value of the peak amplitude of the freestanding portion while vibrating at or near the resonant frequency and comparing the measured value of the peak amplitude with a stored peak amplitude value;
comparing an amplitude-versus-frequency plot of the freestanding portion with a stored amplitude-versus-frequency plot; or
measuring and comparing values of peak amplitudes at two or more resonant nodes while vibrating the freestanding portion at or near the resonant frequency.

21. A method according to claim 20, wherein the step of ascertaining the damping effect further comprises calculating the value of the quality factor of the freestanding portion while vibrating at or near the resonant frequency and comparing the calculated value of the quality factor with a stored quality factor value.

22. A method according to claim 20, wherein the damping effect is ascertained by measuring the value of the peak amplitude of the freestanding portion while vibrating at or near the resonant frequency and comparing the measured value of the peak amplitude with the stored peak amplitude value.

23. A method according to claim 20, wherein the damping effect is ascertained by comparing the amplitude-versus-frequency plot of the freestanding portion with the stored amplitude-versus-frequency plot.

24. A method according to claim 20, wherein the damping effect is ascertained by measuring and comparing the values of peak amplitudes at the two or more resonant nodes while vibrating the freestanding portion at or near the resonant frequency.

25. A method according to claim 20, wherein the assessing step includes estimating the viscosity of the fluid.

26. A method according to claim 20, further comprising collecting and storing a first set of data pertaining to the movement of the freestanding portion at or near the resonant frequency, and then comparing the first set of data with a second set of data subsequently collected while vibrating the freestanding portion at or near the resonant frequency.

27. A method according to claim 20, wherein the assessing step is performed intermittently to assess the viscosity of the fluid within the tube.

28. A method according to claim 20, wherein the assessing step is performed continuously to assess the viscosity of the fluid within the tube.

29. A method according to claim 20, wherein the fluid flows through the tube during the assessing step.

30. A method according to claim 29, further comprising determining the mass flow rate of the fluid flowing through the tube by sensing a Coriolis force-induced twisting of the freestanding portion of the tube.

31. A method according to claim 29, further comprising determining the density of the fluid flowing through the tube by sensing changes in the resonant frequency of the freestanding portion of the tube.

32. A method according to claim 20, wherein the fluid does not flow through the tube during the assessing step.

33. A method according to claim 20, further comprising sensing the temperature of the fluid in the freestanding portion of the tube.

34. A method according to claim 20, further comprising the step of micromachining the freestanding portion of the tube to be a cantilevered portion of the tube above a surface of a substrate supporting the tube.

35. A method according to claim 34, wherein the freestanding portion of the tube is micromachined to contain flow turbulators that extend into the passage within the freestanding portion of the tube.

36. A method according to claim 20, further comprising hermetically bonding a cap to the substrate so as to define a hermetically-sealed evacuated enclosure containing the freestanding portion of the tube.

37. A method according to claim 20, wherein the tube is formed of semiconducting material.

38. A method according to claim 20, wherein the fluid flows through the tube during the assessing step, and the method further comprises determining the mass flow rate of the fluid flowing through the tube by sensing a Coriolis force-induced twisting of the freestanding portion of the tube, determining the density of the fluid flowing through the tube by sensing changes in the resonant frequency of the freestanding portion of the tube, and sensing the temperature of the fluid in the freestanding portion of the tube.

39. A method according to claim 38, wherein the tube is a component of a lubrication system, the fluid is a lubricant, and the viscosity, the mass flow rate, the density, and the temperature of the lubricant are used to indicate the condition of the lubricant and the lubrication system.

* * * * *